US010335132B2

United States Patent
Aogi et al.

(10) Patent No.: US 10,335,132 B2
(45) Date of Patent: Jul. 2, 2019

(54) RETRACTOR

(71) Applicants: National Hospital Organization, Tokyo (JP); OZK CO., LTD., Yao-shi, Osaka (JP); Shinwa Syoji CO., LTD., Higashiosaka-shi, Osaka (JP)

(72) Inventors: Kenjiro Aogi, Matsuyama (JP); Haruhiko Yamasaki, Yao (JP); Katsunori Mitsuhashi, Higashiosaka (JP); Yoshiro Morishita, Higashiosaka (JP)

(73) Assignees: NATIONAL HOSPITAL ORGANIZATION, Tokyo (JP); OZK CO., LTD., Yao-shi (JP); SHINWA SYOJI CO., LTD., Higashiosaka-shi (JP)

( * ) Notice: Subject to any disclaimer, the term of this patent is extended or adjusted under 35 U.S.C. 154(b) by 149 days.

(21) Appl. No.: 15/545,838

(22) PCT Filed: Oct. 14, 2015

(86) PCT No.: PCT/JP2015/079045
§ 371 (c)(1),
(2) Date: Jul. 24, 2017

(87) PCT Pub. No.: WO2016/121169
PCT Pub. Date: Aug. 4, 2016

(65) Prior Publication Data
US 2018/0000474 A1 Jan. 4, 2018

(30) Foreign Application Priority Data

Jan. 29, 2015 (JP) ................................. 2015-015622

(51) Int. Cl.
*A61B 17/02* (2006.01)
*A61B 17/00* (2006.01)

(52) U.S. Cl.
CPC .......... *A61B 17/02* (2013.01); *A61B 17/0293* (2013.01); *A61B 2017/00862* (2013.01);
(Continued)

(58) Field of Classification Search
CPC ................ A61B 17/02; A61B 17/0293; A61B 2017/00884; A61B 2017/00862
See application file for complete search history.

(56) References Cited

U.S. PATENT DOCUMENTS

| 5,375,481 A | 12/1994 | Cabrera |
| 2004/0054353 A1 | 3/2004 | Taylor |

(Continued)

FOREIGN PATENT DOCUMENTS

| JP | H06-055607 A | 3/1994 |
| JP | H07-239727 A | 9/1995 |

(Continued)

OTHER PUBLICATIONS

"Koppel Single Hook/Koppel Double Hook" list, Tanaka Medical Instrument Co., Ltd., Internet URL: http://www.e-tanaka.co.jp/products/display_detail/23-18-G_19-G; 1 Sheet/p. 3 of specification.

(Continued)

*Primary Examiner* — Christian A Sevilla
(74) *Attorney, Agent, or Firm* — Kratz, Quintos & Hanson, LLP

(57) ABSTRACT

Provided is a retractor that makes it possible to reduce operation costs, is less likely to cause damage to surgical incision sites, do not reduce workability, and also makes it possible to easily maintain the desired surgical field and to change the surgical field or widen or narrow the area of the surgical field, depending on the surgical situation. The retractor 1 for holding a surgical incision open and maintaining a surgical field during an operation includes a belt-shaped body A made of a wire; and a connecting part B (Continued)

that is provided at one end portion of the belt-shaped body A and capable of being connected to another end portion or an intermediate portion of the belt-shaped body A so that the belt-shaped body A can be formed into a loop of a desired size. The retractor 1 is so configured that when the belt-shaped body A is formed into a loop, the outer surface of the belt-shaped body A resists the force generated at the surgical incision and acting in such a direction as to close the surgical incision.

6 Claims, 8 Drawing Sheets

(52) U.S. Cl.
CPC ............ *A61B 2017/00884* (2013.01); *A61B 2017/00991* (2013.01); *A61B 2017/0225* (2013.01)

(56) References Cited

U.S. PATENT DOCUMENTS

| | | | | |
|---|---|---|---|---|
| 2005/0090717 | A1* | 4/2005 | Bonadio | A61B 17/0293 600/208 |
| 2012/0078057 | A1* | 3/2012 | Scott | A61B 17/0218 600/201 |
| 2012/0289785 | A1 | 11/2012 | Albrecht | |
| 2013/0018229 | A1 | 1/2013 | Jaworek | |

FOREIGN PATENT DOCUMENTS

| | | |
|---|---|---|
| JP | 2005-506144 A1 | 3/2005 |
| JP | 2006-304819 A1 | 11/2006 |
| JP | 2007-082674 A1 | 4/2007 |
| JP | 2013-055993 A1 | 3/2013 |
| JP | 2014-519883 A1 | 8/2014 |
| WO | 2007083305 A2 | 7/2007 |
| WO | 2009034922 A1 | 3/2009 |

OTHER PUBLICATIONS

"Octopus Universal Retractor" list, Yufu Itonaga Co., Ltd., Nov. 2012, Internet URL: http://www.yufu.co.jp/pdf/octopus.pdf (Cover sheet, pp. 1-14, end sheet, 16 Sheets total)/p. 3 of specification.

"Table Mounted Retractor System" list, Solve Corporation, Internet URL: http://www.solve-net.com/MakerBusiness/Surgical/img_Medifiex/RetractorProducts.pdf; (Two cover sheets, pp. 1-37, end sheet, 40 pages total)/p. 3 of specification.

International Search Report for International Application No. PCT/JP2015/079045 dated Jan. 12, 2016.

* cited by examiner

RETRACTOR

TECHNICAL FIELD

The present invention relates to a retractor for holding a surgical incision open and maintaining a surgical field during an operation.

BACKGROUND ART

During a manual operation on an affected area, the surgical incision must be held open so that the surgical field can be maintained and the surgeon can reach the affected area, because the force generated at the surgical incision acts in such a direction as to close the surgical incision. Maintaining the surgical field in a good condition makes it possible, for example, to reduce the operation time, to improve the safety, and to reduce fatigue of the operator (surgeon).

In a common method for holding a surgical incision open, surgical assistants hold rod-shaped medical devices with hooked front ends (see, for example, Non Patent Literature 1) and pull, by hand, the medical devices with the front ends hooked on the surgical incision site (hereinafter, this method will be referred to as "the method of holding the surgical incision open by hand").

Other methods include using retractors whose front ends are hooked on the surgical incision site and which are held with an articulated arm extending from a pole (see, for example, Patent Literatures 1 and 2); and using retractors whose front ends are hooked on the surgical incision site and which are held with a support ring, an arm, and a pole (see, for example, Patent Literature 2 and Non Patent Literature 3) (hereinafter, these methods will be referred to as "the method of holding the surgical incision open with arm support type retractors").

Further proposed methods include providing a retractor including in-body-side and out-body-side ring members fixed on both peripheral edges of the opening of a tubular flexible sleeve and bringing the outer surface of the flexible sleeve of the retractor into contact with the surgical incision site (see, for example, Patent Literature 3); and providing a retractor made of a rectangular elastic sheet, winding the retractor into a small-diameter roll with its beginning and terminal ends slidable relatively to each other, inserting the small-diameter roll into the surgical incision by hand, and then releasing the roll from hand so that the roll expands in diameter due to the elastic force to widen the surgical incision (see, for example, Patent Literature 4) (hereinafter, these methods will be referred to as "the method of holding the surgical incision open with an independent type retractor").

CITATIONS LIST

Patent Literatures

Patent Literature 1: Japanese Unexamined Utility Model Application Publication No. H06-55607
Patent Literature 2: Japanese Unexamined Patent Application Publication No. H07-239727
Patent Literature 3: Japanese Unexamined Patent Application Publication No. 2013-55993
Patent Literature 4: Japanese Translation of PCT International Application Publication No. 2007-82674

Non Patent Literatures

Non Patent Literature 1: "Koppel Single Hook/Koppel Double Hook" list, Tanaka Medical Instrument Co., Ltd., Internet URL: http://www.e-tanaka.co.jp/products/display_detail/23-18-G_19-G
Non-Patent Literature 2: "Octopus Universal Retractor" list, Yufu Itonaga Co., Ltd., November 2012, Internet URL: http://www.yufu.co.jp/pdf/octopus.pdf
Non-Patent Literature 3: "Table Mounted Retractor System" list, Solve Corporation, Internet URL: http://www.solve-net.com/MakerBusiness/Surgical/img_Mediflex/RetractorProducts.pdf

SUMMARY OF INVENTION

Technical Problems

In the method of holding the surgical incision open by hand, a required number of surgical assistants have to hold and pull, by hand, a required number of the medical devices with the front ends hooked on the surgical incision site. Therefore, this method will be more likely to cause damage to the surgical incision site, on which the front ends of the medical devices hooked, and can place a relatively large burden on the surgical assistants and increase the operation costs due to the assistant labor costs.

The method of holding the surgical incision open with arm support type retractors can eliminate the need for surgical assistants to hold and pull the medical devices, and thus can reduce the labor costs as compared with the method of holding the surgical incision open by hand.

However, the method, in which the retractors are pulled while their front ends are hooked on the surgical incision site, will also be more likely to cause damage to the surgical incision site.

In addition, the retractors form a relatively large system, which increases the retractor production costs and accordingly increases the operation costs.

In addition, the pole, arm, and other parts may become an encumbrance to the operator and reduce the workability, and will also make it impossible to flexibly change the surgical field depending on the surgical situation.

The method of holding the surgical incision open with an independent type retractor can eliminate the need for assistants to hold and pull the medical devices and thus reduce the labor costs as compared with the method of holding the surgical incision open by hand. In addition, the retractor free of any additional part such as an arm or a pole will not become an encumbrance to the operator or reduce the workability in contrast to the arm support type retractor for holding the surgical incision open.

In that method, however, the surgical field cannot be changed depending on the surgical situation, and the area of the surgical field cannot be widened or narrowed depending on the surgical situation.

In addition, the method of holding the surgical incision open with an independent type retractor configured as described in Patent Literature 3 requires a laborious process to put the retractor in place in such a manner that the outer surface of the flexible sleeve is in the contact with the surgical incision site.

In addition, the method of holding the surgical incision open with at independent type retractor configured as described in Patent Literature 4 may fail to maintain the desired surgical field, because the elastic force is used to expand the diameter of the roll and to widen the surgical incision, which may fail to produce the force necessary to hold the surgical incision open.

In view of the above circumstances, an object of the present invention is to provide a retractor that makes it possible to reduce operation costs, is less likely to cause damage to surgical incision sites, do not reduce workability, and also makes it possible to easily maintain the desired surgical field, to change the surgical field depending on the surgical situation, and to widen or narrow the area of the surgical field depending on the surgical situation.

Solutions to Problems

To solve the above problems, the present invention is directed to a retractor for holding a surgical incision open and maintaining a surgical field during an operation, the retractor including: a belt-shaped body made of a wire; and a connecting part that is provided at one end portion of the belt-shaped body and capable of being connected to another end portion or an intermediate portion of the belt-shaped body so that the belt-shaped body can be formed into a loop of a desired size, the retractor being so configured that when the belt-shaped body is formed into a loop, the outer surface of the belt-shaped body resists the force generated at the surgical incision and acting in such a direction as to close the surgical incision.

According to these features, the outer surface of the belt-shaped body looped with the connecting part resists the force acting in such a direction as to close the surgical incision, which eliminates the need for surgical assistants to pull and hold rod-shaped medical devices with hooked front ends. This makes it possible to reduce labor costs, as pared with the method of holding the surgical incision open by hand, and to make immediate intervention even when a temporary or emergency operation needs to be performed by only one doctor, for example, in accident and emergency situations.

Moreover, when the retractor of the present invention is used, the surgical incision site does not need to be hooked on the front ends of the rod-shaped medical devices or any other retractors or pulled with the rod-shaped medical devices or any other retractors, so that the surgical incision site will not be damaged in contrast to the method of holding the surgical incision open by hand and the method of holding the surgical incision open with arm support type retractors.

Furthermore, the retractor of the present invention is free of any obstructive part such as an arm or a pole and thus will not reduce workability in contrast to the arm support type retractor for holding the surgical incision open.

In addition, the retractor of the present invention has a simple structure including the belt-shaped body made of a wire; and the connecting part provided to allow the belt-shaped body to be formed into a loop. Therefore, the retractor of the present invention can be produced at a lower cost than the arm support type retractor for holding the surgical incision open.

In addition, the connecting part allows the belt-shaped body to be formed into a loop of a desired size. This makes it possible to easily maintain the desired surgical field, as compared with the method of holding the surgical incision open with a conventional independent type retractor. This also makes it possible to easily change the surgical field or easily widen or narrow the area of the surgical field, depending on the surgical situation.

In addition, the belt-shaped body is made of a wire. Therefore, in contrast to the conventional independent type retractor for holding the surgical incision open, the retractor of the present invention can be used not only in a circular loop shape but also in an elliptical, oval, or any other shape to maintain the desired surgical field, and additionally, the belt-shaped body can also be deformed in the transverse direction, so that the retractor of the present invention can be deformed or displaced so as not to cause any damage to lower bones, muscles, blood vessels, or other sites.

In the retractor of the present invention, the belt-shaped body is preferably a product obtained by pressurizing and plastically deforming a coil spring.

According to this feature, the belt-shaped body made of a wire can be produced by subjecting a coil spring, which is easily formed using a spring coiling machine (coiling machine) other means, to pressurization and plastic deformation, in which, for example, the coil spring is passed between rolls, so that the retractor of the present invention can be produced at a lower cost.

In addition, the belt-shaped body formed by pressurizing and plastically deforming a coil spring maintains smooth surfaces (upper and lower surfaces and outer and inner surfaces) even when the loop size is changed. Therefore, the belt-shaped body will not cause any damage to patient's internal organs and other body parts or to operator's gloves.

In addition, the coil spring preferably has a pitch greater than its wire diameter.

According to this feature, a gap is formed between the turns of the coil. This makes easy the process of forming the belt-shaped body by pressurization and plastic deformation and also makes the looped retractor easily deformable. Therefore, this feature makes it easy to change the surgical field, depending on the surgical situation, and to avoid any damage to lower bones, muscles, blood vessels, or other sites.

In addition, the belt-shaped body made of a wire can provide a high unoccupied space ratio, so that relatively large gaps can be formed in belt-shaped body formed into a loop. The gaps make it easy to see the surgical site and its surroundings during the operation, so that the workability can be improved.

In addition, the belt-shaped body is more preferably a product obtained by pressurizing and plastically deforming a coil spring assembly that is obtained by inserting, into each other, a pair of left- and right-hand coil springs each having a pitch greater than its wire diameter.

According to this feature, the belt-shaped body is formed by inserting a pair of left- and right-hand coil springs into each other to form a coil spring assembly and then pressurizing and plastically deforming the coil spring assembly. In this case, therefore, even when a lightweight, less stiff wire is used for ease of handling and other purposes, it is easy to form the belt-shaped body with sufficient stiffness required to resist the force acting in such a direction as to close the surgical incision and required to hold the surgical incision open.

In addition, the use of a pair of left- and right-hand coil springs makes easy the process of forming the coil spring assembly by insertion into each other and also makes it possible to suppress the increase in production cost because the pair of coil springs can be easily produced using a spring coiling machine (coiling machine) or other means.

In addition, the retractor more preferably further includes a plurality of hooks that are provided apart from one another in a circumferential direction on the outer surface of the belt-shaped body formed into a loop, the hooks being so provided that the skin around the surgical incision can be held on the hooks.

According to this feature, the skin around the surgical incision can be reliably held on the hooks so that the surgical incision can be prevented from shifting. This makes it possible to prevent unintentional movement of the surgical incision, which might otherwise interfere with the operation, to prevent surgical instruments or other tools from coming into incidental contact with and injuring non-affected areas, and to efficiently perform the operation while the surgical field is surely maintained.

In addition, the belt-shaped body formed into a loop more preferably has an outer surface that has been roughened to have an increased friction coefficient.

According to this feature, the outer surface of the belt-shaped body has been roughened to have an increased friction coefficient, which provides an anti-skid function to prevent the surgical incision from shifting when the skin around the surgical incision comes into contact with the outer surface of the belt-shaped body. This makes it possible to prevent unintentional movement of the surgical incision, which might otherwise interfere with the operation, to prevent surgical instruments or other tools from coming into incidental contact with and injuring non-affected areas, and to efficiently perform the operation while the surgical field is surely maintained.

Advantageous Effects of Invention

As described above, the retractor according to the present invention has, for example, the following significantly advantageous effects.

(1) The outer surface of the belt-shaped body looped with the connecting part resists the force acting in such a direction as to close the surgical incision, which makes it possible to reduce labor costs, to make immediate intervention even when a operation needs to be performed by only one doctor, for example, in accident and emergency situations, and to prevent any damage to the surgical incision site.

(2) The retractor is free of any obstructive part such as an arm or a pole and thus will not reduce workability.

(3) The retractor can be produced at a lower cost because it has a simple structure including the belt-shaped body made of a wire; and the connecting part provided to allow the belt-shaped body to be formed into a loop.

(4) The connecting part allows the belt-shaped body to be formed into a loop of a desired size, which makes it possible to easily maintain the desired surgical field and to easily change the surgical field or easily widen or narrow the area of the surgical field, depending on the surgical situation.

(5) The belt-shaped body made of a wire can be deformed to maintain any desired surgical field and can also be deformed in the transverse direction, so that the retractor can be deformed or displaced so as not to cause any damage to lower bones, muscles, blood vessels, or other sites.

(6) The belt-shaped body made of a wire can be produced by pressurizing and plastically deforming a coil spring, which makes it possible to reduce the production cost and allows the belt-shaped body to maintain smooth surfaces (upper and lower surfaces and outer and inner surfaces) even when the loop size is changed, so that the belt-shaped body will not cause any damage to patient's internal organs and other body parts or to operator's gloves.

(7) The use of a coil spring with a pitch greater than its wire diameter makes easy the process of forming the belt-shaped body and also makes it easy to deform the looped detractor, which allows easy change of the surgical field depending on the surgical situation and also allows easy avoidance of damage to lower bones, muscles, blood vessels, or other sites, and in this case, relatively large gaps formed in the belt-shaped body formed into a loop make it easy to see the surgical site and its surroundings during the operation, so that the workability can be improved.

(8) In the case where the belt-shaped body made of a wire is produced by pressuring and plastically deforming a coil spring assembly that is formed by inserting, into each other, a pair of left- and right-hand coil springs each with the pitch greater than the wire diameter, it is easy to form the belt-shaped body with sufficient stiffness required to resist the force acting in such a direction as to close the surgical incision and required to hold the surgical incision open, even when a lightweight, less stiff wire is used for ease of handling and other purposes, and the increase in production cost can also be suppressed.

(9) When the retractor further includes a plurality of hooks that are provided apart from one another in a circumferential direction on the outer surface of the belt-shaped body formed into a loop and also so provided that the skin around the surgical incision can be held on the hooks, or when the belt-shaped body has an outer surface that has been roughened to have an increased friction coefficient, the retractor can prevent the surgical incision from shifting, which makes it possible to prevent unintentional movement of the surgical incision, which might otherwise interfere with the operation, to prevent surgical instruments or other tools from coming into incidental contact with and injuring non-affected areas, and to efficiently perform the operation while the surgical field is surely maintained.

DESCRIPTION OF EMBODIMENTS

Next, embodiments of the present invention will be described in detail with reference to the attached drawings. It will be understood that the present invention is not limited to the embodiments shown in the attached drawings and encompasses all possible embodiments satisfying the requirements recited in the claims.

Figure 1:
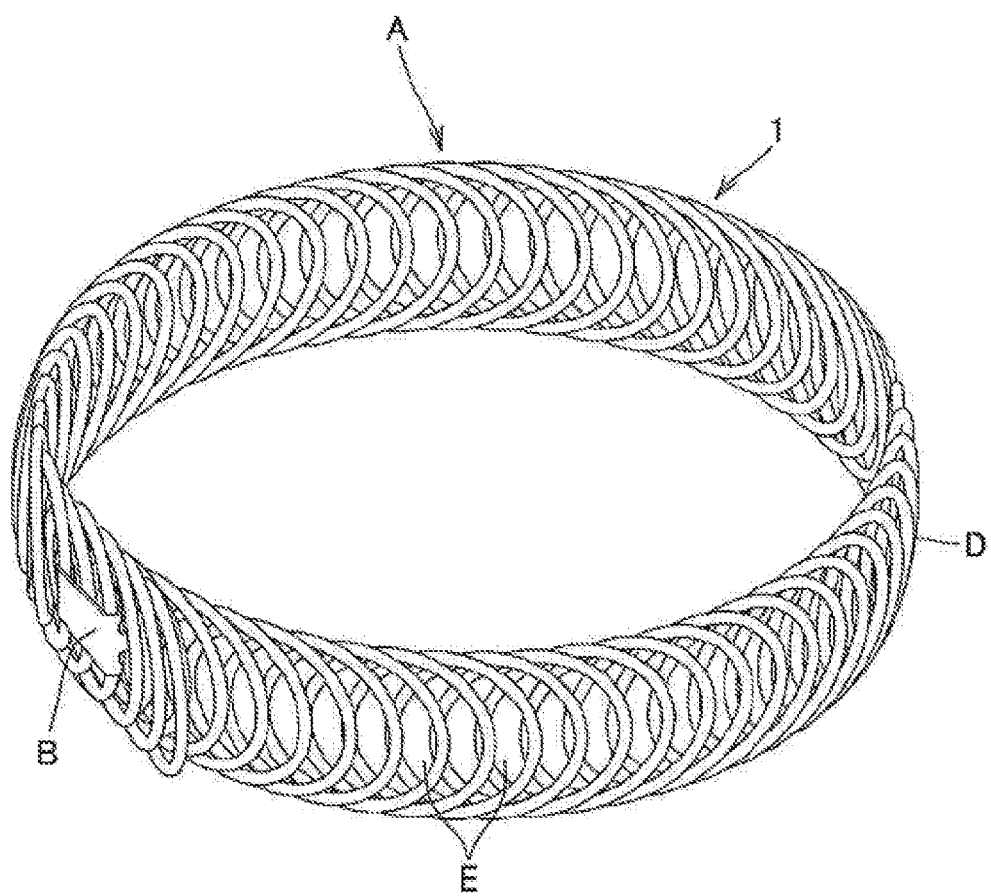
FIG. 1 is a perspective view showing an example of how to use a retractor according to an embodiment of the present invention looped with a connecting part.
Figure 2:
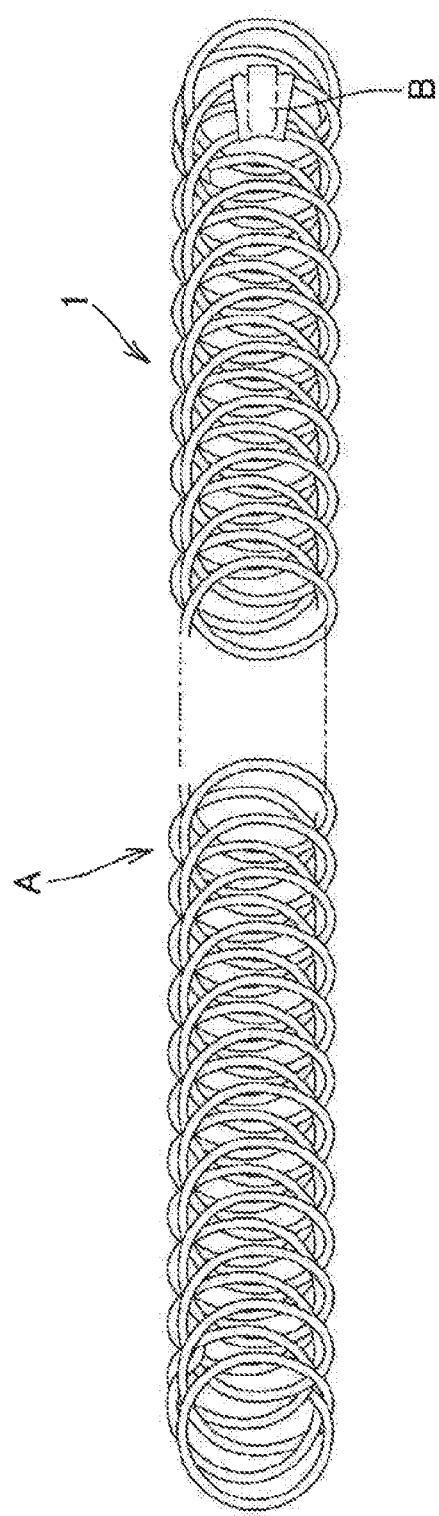
FIG. 2 is a front view showing the retractor according to an embodiment of the present invention extended in a belt shape.

FIG. 1 is a perspective view showing an example of how to use a retractor 1 according to an embodiment of the present invention. FIG. 2 is a front view showing the retractor 1 extended in a belt shape. As shown in FIGS. 1 and 2, the retractor 1, which is for holding a surgical incision open and maintaining a surgical field during an operation, includes a belt-shaped body A made of a wire; and a connecting part B that is provided at one end portion of the belt-shaped body A and capable of being connected to another end portion or an intermediate portion of the belt-shaped body A so that the belt-shaped body A can be formed into a loop of a desired size. In addition, the retractor 1 is so configured that when the belt-shaped body A is formed into a loop as shown in FIG. 1, the outer surface D of the belt-shaped body A resists the force generated at the surgical incision and acting in such a direction as to close the surgical incision.

In this embodiment, the wire used to form the belt-shaped body A is a wire of a metal such as pure titanium, a titanium alloy, an aluminum alloy, a copper alloy, or stainless steel, a wire of a super-elastic alloy such as a nickel-titanium alloy or a copper-based alloy, or a wire of synthetic resin such as polyethylene terephthalate (PET) resin, polyamide (PA) resin, or polyether ether ketone (PEEK) resin (optionally containing reinforcing fibers such as glass fibers or carbon fibers). The cross-sectional shape of the wire is circular, as in this embodiment, or polygonal.

The connecting part B is made of a metal such as stainless steel or synthetic resin such as PET resin.

Figure 3:
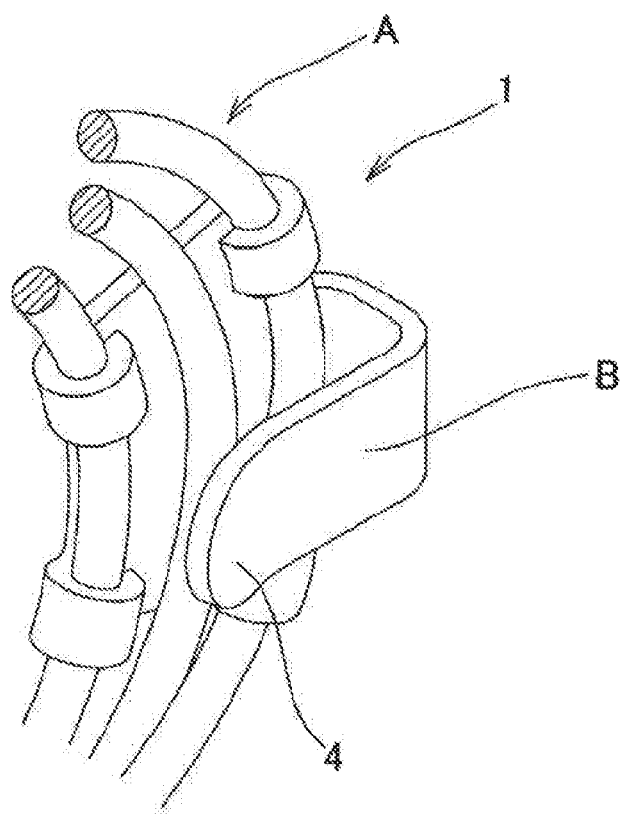
FIG. 3 is an enlarged perspective view of a main part at and around a connecting part.

As shown in the main part enlarged perspective view of FIG. 3, the connecting part B provided at one end portion of the belt-shaped body A has a hook 4. Therefore, the belt-shaped body A can be easily formed into a loop of a desired size by hooking the hook 4 on another end portion or an intermediate portion of the wire of belt-shaped body A, and the size of the loop can also be easily changed by hooking the hook 4 on the wire.

It will be understood that FIG. 3 is not intended to limit the shape or structure of the connecting part B and that the connecting part B may have any other shape or structure that allows one end portion of the belt-shaped body A to be connected to and disconnected from another end portion or an intermediate portion of the belt-shaped body A.

Next, an example of a method for producing the belt-shaped body A of the retractor 1 will be described.

Figure 4:
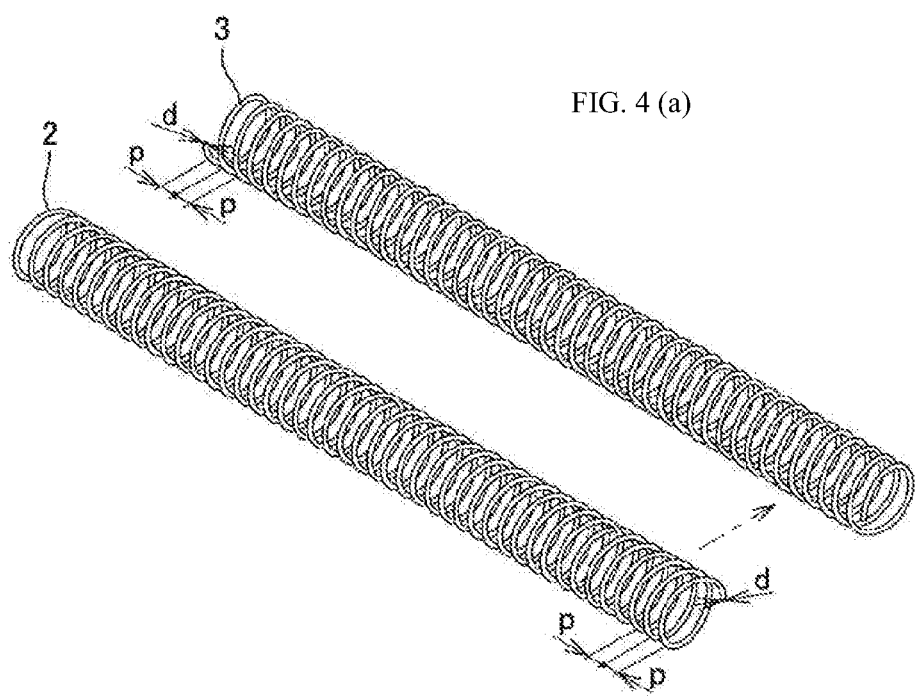
FIG. 4(a) is a perspective view of left- and right-hand coil springs.
FIG. 4(b) is a perspective view of a coil spring assembly.
Figure 4:
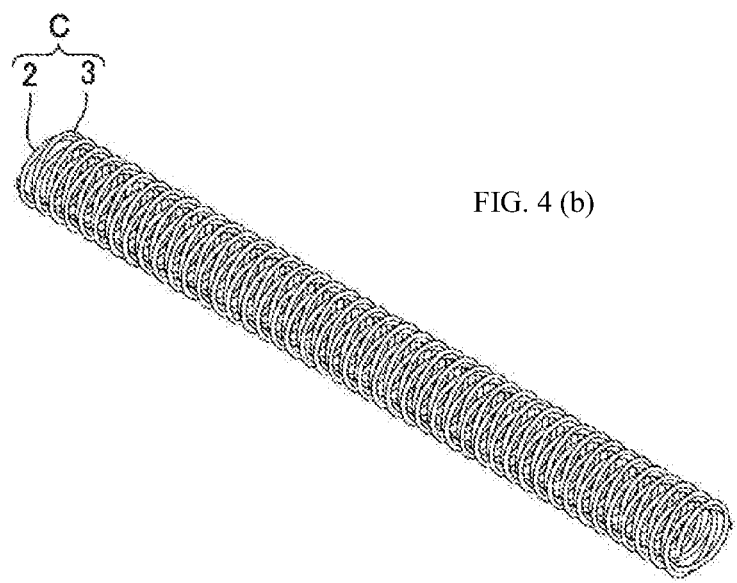

First, as shown in the perspective view of FIG. 4(*a*), compression springs with a specific wire diameter d, a specific pitch p, a specific outer diameter, and a specific number of turns are formed using a spring coiling machine (coiling machine) or other means, so that a pair of left- and right-hand coil springs 2 and 3 are prepared, each with the pitch p greater than the wire diameter d (d<p).

Subsequently, as shown in the perspective view of FIG. 4(*b*), the left- and right-hand coil springs 2 and 3 are inserted into each other (combined) to form a coil spring assembly C. In this process, the coil springs 2 and 3 with different winding directions can be easily inserted into each other.

Subsequently, as shown in the schematic diagram of FIG. 5, the coil spring assembly C is plastically deformed by being passed between a pair of rolls R1 and R2 to form the belt-shaped body A.

Figure 5:
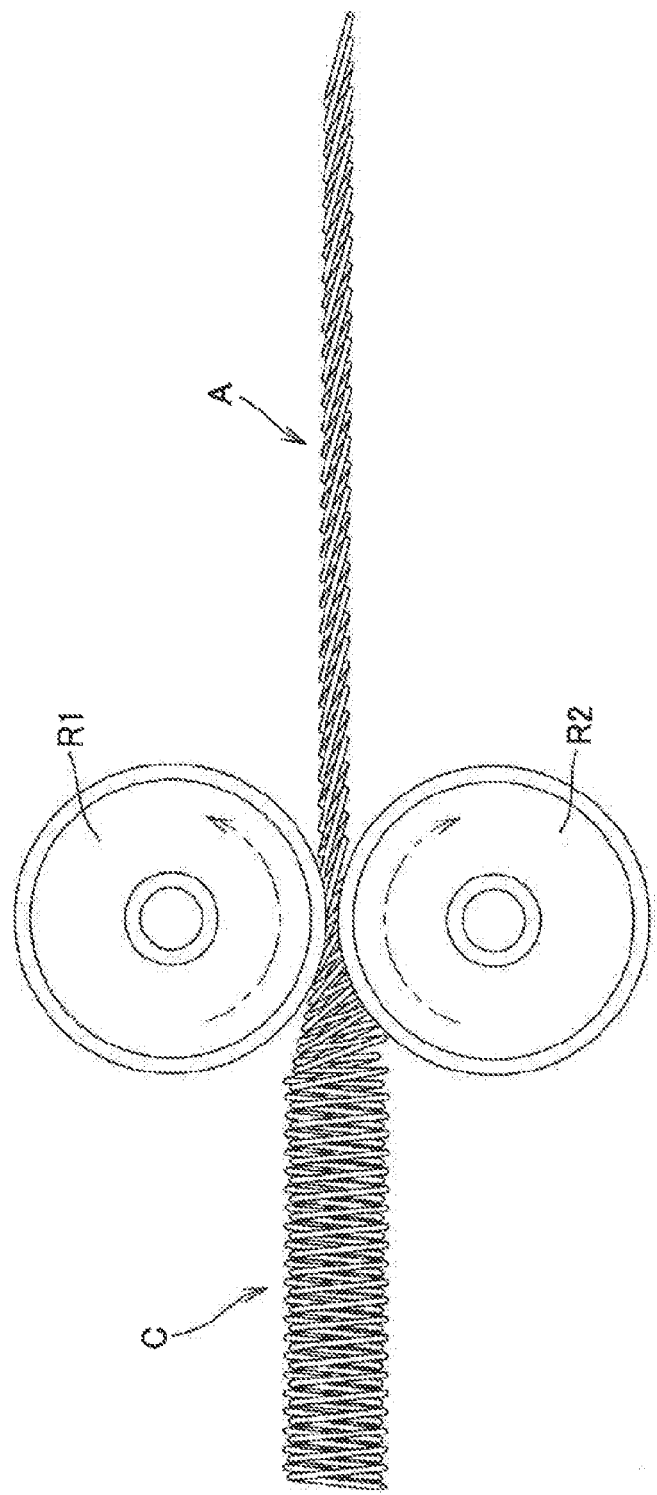
FIG. 5 is a schematic diagram showing the process of forming a coil spring assembly into a belt-shaped body by plastic deformation in which the coil spring assembly is passed between a pair of rolls.

Alternatively, the process of plastically deforming the coil spring assembly C to form the belt-shaped body A may be performed using, for example, a press mold instead of the pair of rolls R1 and R2 shown in FIG. 5. However, the production cost can be reduced using the pair of rolls R1 and R2.

Subsequently, the connecting part B is attached to one end portion of the belt-shaped body A so that the retractor 1 is completed.

Figure 6:
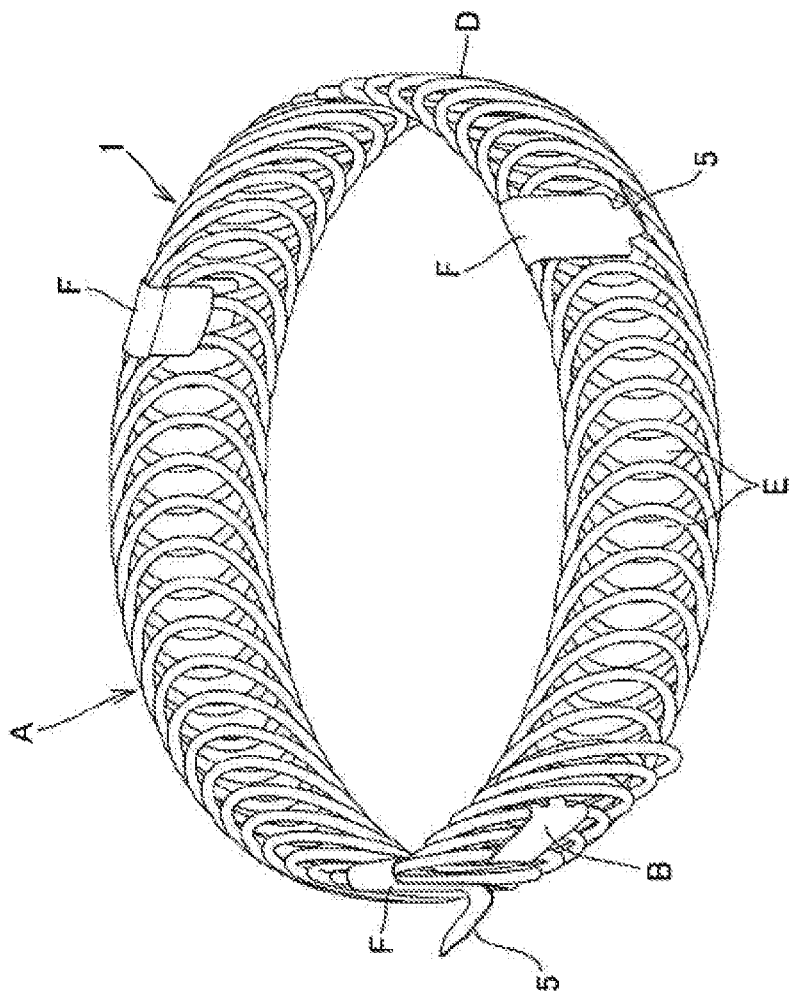
FIG. 6(a) is a perspective view showing a retractor provided with hooks on which the skin around a surgical incision is to be held.
FIG. 6(b) is a perspective view of the hook.
Figure 6:
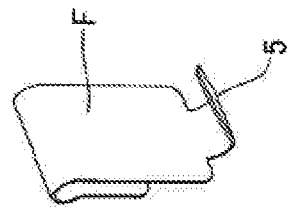

As shown in the perspective views of FIGS. 6(*a*) and 6(*b*), the loop of the belt-shaped body A of the retractor 1 (see FIGS. 1 and 2) completed as described above may be provided with a plurality of hooking parts F (three hooking parts F in this embodiment), which are spaced in the circumferential direction and on which the skin around a surgical incision is to be held. In this embodiment, the hooking parts F are made of a metal such as stainless steel or synthetic resin such as PET resin.

According to this feature, the outer surface D of the belt-shaped body A formed into a loop is provided with hooks 5 protruding outside in the radial direction from the hooking parts F spaced in the circumferential direction. Therefore, the skin around the surgical incision can be reliably held on the hooks 5 so that the surgical incision can be prevented from shifting. This makes it possible to prevent unintentional movement of the surgical incision, which might otherwise interfere with the operation, to prevent surgical instruments or other tools from coming into incidental contact with and injuring non-affected areas, and to efficiently perform the operation while the surgical field is surely maintained.

Alternatively, without the hooking parts F shown in FIG. 6(*a*), the friction coefficient of the outer surface D may be increased by, for example, shot blasting in which the outer surface D of the loop of the belt-shaped body A of the retractor 1 shown in FIG. 1 is roughened by allowing particles called projectiles to collide with the outer surface D.

This feature also makes it possible to prevent displacement of the surgical incision and thus makes it possible to prevent unintentional movement of the surgical incision, which might otherwise interfere with the operation, to prevent surgical instruments or other tools from coming into incidental contact with and injuring non-affected areas, and to efficiently perform the operation while the surgical field is surely maintained.

The above description has shown a case where the coil springs 2 and 3 have a circular coil shape. Alternatively, however, the coil may have a non-circular shape such as an elliptical shape.

Figure 7:
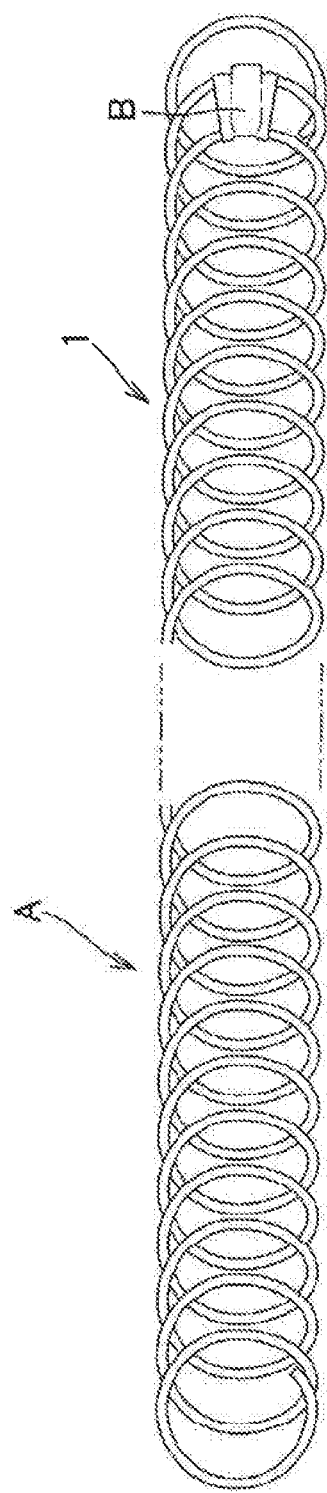
FIG. 7 is a front view showing a retractor according to a modified embodiment extended in a belt shape.

The above description has also shown a case where the belt-shaped body A used to form the retractor 1 is produced using a pair of left- and right-hand coil springs 2 and 3. Alternatively, however, the belt-shaped body A shown in the front view of FIG. 7 may also be used, which is produced by pressurizing and plastically deforming one of left- and right-hand coil springs.

Figure 8:
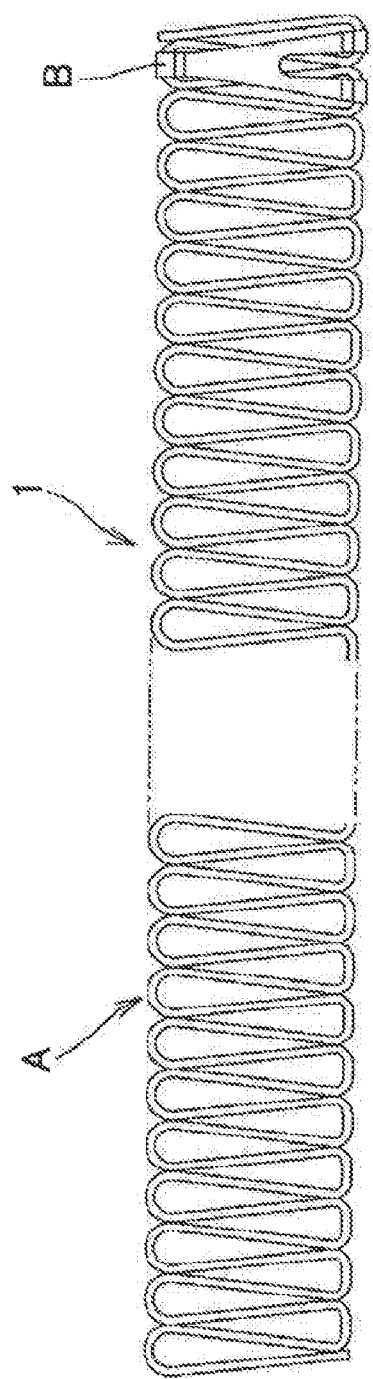
FIG. 8 is a front view showing a retractor according to another modified embodiment extended in a belt shape.

In addition, the belt-shaped body A used to form the retractor 1 may also be a belt-shaped body A having a repeating structure as shown in the front view of FIG. 8, which is formed by extending and shaping a wire in a plane instead of pressuring and plastically deforming a coil spring.

When the retractor 1 with the features described above is used, the outer surface D of the belt-shaped body A looped with the connecting part B resists the force acting in such a direction as to close the surgical incision. Therefore, the use of the retractor 1 eliminates the need for surgical assistants to hold and pull rod-shaped medical devices with a hooked front end. This makes it possible to reduce labor costs, as compared with the method of holding the surgical incision open by hand, and to make immediate intervention even when a temporary or emergency operation needs to be performed by only one doctor, for example, in accident and emergency situations.

Moreover, when the retractor 1 is used, the surgical incision site does not need to be hooked on the front ends of the rod-shaped medical devices or any other retractors or pulled with the rod-shaped medical devices or any other retractors, so that the surgical incision site will not be damaged in contrast to the method of holding the surgical incision open by hand and the method of holding the surgical incision open with arm support type retractors.

Furthermore, the retractor 1 is free of any obstructive part such as an arm or a pole and thus will not reduce workability in contrast to the arm support type retractor for holding the surgical incision open.

In addition, the retractor 1 has a simple structure including the belt-shaped body A made of a wire; and the connecting part B provided to allow the belt-shaped body A to be formed into a loop. Therefore, the retractor 1 can be produced at a lower cost than the arm support type retractor for holding the surgical incision open.

In addition, the connecting part B allows the belt-shaped body A to be formed into a loop of a desired size. This makes it possible to easily maintain the desired surgical field, as compared with the method of holding the surgical incision open with a conventional independent type retractor. This also makes it possible to easily change the surgical field or easily widen or narrow the area of the surgical field, depending on the surgical situation.

In addition, the belt-shaped body A is made of a wire. Therefore, in contrast to the conventional independent type retractor for holding the surgical incision open, the retractor 1 can be used not only in a circular loop shape but also in an elliptical, oval, or any other shape to maintain the desired surgical field, and additionally, the belt-shaped body A can also be deformed in the transverse direction, so that the retractor 1 can be deformed or displaced so as not to cause any damage to lower bones, muscles, blood vessels, or other sites.

In addition, the belt-shaped body A can be produced by pressurizing and plastically deforming a coil spring. In this case, the belt-shaped body A made of a wire can be produced by subjecting a coil spring, which is easily formed using a spring coiling machine (coiling machine) or other means, to pressurization and plastic deformation, in which, for example, the coil spring is passed between rolls, so that the retractor 1 can be produced at a lower cost.

In addition, the belt-shaped body A formed by pressurizing and plastically deforming a coil spring maintains smooth surfaces (upper and lower surfaces and outer and inner surfaces) even when the loop size is changed. Therefore, the belt-shaped body A will not cause any damage to patient's internal organs and other body parts or to operator's gloves.

In addition, when the coil spring has a pitch p greater than its wire diameter d, a gap is formed between the turns. This feature makes easy the process of forming the belt-shaped body by pressurization and plastic deformation and also makes the looped retractor 1 easily deformable. Therefore, this feature makes it easy to change the surgical field, depending on the surgical situation, and to avoid any damage to lower bones, muscles, blood vessels, or other sites. In addition, the belt-shaped body A made of a wire can provide a high unoccupied space ratio, so that relatively large gaps E (see FIG. 1) can be formed in the belt-shaped body A formed into a loop. The gaps E make it easy to see the surgical site and its surroundings during the operation, so that the workability can be improved.

In addition, the belt-shaped body A can be formed by inserting, into each other, a pair of left- and right-hand coil springs 2 and 3 each with the pitch p greater than the wire diameter d to form a coil spring assembly C and then pressuring and plastically deforming the coil spring assembly C. In this case, even when a lightweight, less stiff wire (such as an aluminum alloy wire) is used for ease of handling and other purposes, it is easy to form the belt-shaped body A with sufficient stiffness required to resist the force acting in such a direction as to close the surgical incision and required to hold the surgical incision open.

In addition, the use of a pair of left- and right-hand coil springs 2 and 3 makes easy the process of forming the coil spring assembly C by insertion into each other and also makes it possible to suppress the increase in production cost because the pair of coil springs 2 and 3 can be easily produced using a spring coiling machine (coiling machine) or other means.

REFERENCE SIGNS LIST

1 Retractor
2 Lift-hand coil spring
3 Right-hand coil spring
4, 5 Hook
A Belt-shaped body
B Connecting part
C Coil spring assembly
D Outer surface of belt-shaped body formed into a loop
d Wire diameter
E Gap
F Hooking part
p Pitch
R1, R2 Roll

The invention claimed is:

1. A retractor for holding a surgical incision open and maintaining a surgical field during an operation, the retractor comprising:
a belt-shaped body made of a wire; and
a connecting part that is provided at one end portion of the belt-shaped body and capable of being connected to another end portion or an intermediate portion of the belt-shaped body so that the belt-shaped body can be formed into a loop of a desired size,
the retractor being so configured that when the belt-shaped body is formed into a loop, an outer surface of the belt-shaped body resists a force generated at the surgical incision and acting in such a direction as to close the surgical incision.

2. The retractor according to claim 1, wherein the belt-shaped body is a product obtained by pressurizing and plastically deforming a coil spring.

3. The retractor according to claim 2, wherein the coil spring has a pitch greater than a wire diameter.

4. The retractor according to claim 1, wherein the belt-shaped body is a product obtained by pressurizing and plastically deforming a coil spring assembly that is obtained by inserting, into each other, a pair of left- and right-hand coil springs each having a pitch greater than a wire diameter.

5. The retractor according to claim 1, further comprising a plurality of hooks that are provided apart from one another in a circumferential direction on an outer surface of the belt-shaped body formed into a loop, the hooks being so provided that a skin around the surgical incision can be held on the hooks.

6. The retractor according to claim 1, wherein the belt-shaped body formed into a loop has an outer surface that has been roughened to have an increased friction coefficient.

* * * * *